US00PP20384P2

(12) United States Plant Patent
Kolster

(10) Patent No.: US PP20,384 P2
(45) Date of Patent: Oct. 6, 2009

(54) ***WEIGELA* PLANT NAMED 'KOLMAGIRA'**

(50) Latin Name: *Weigela florida*
Varietal Denomination: Kolmagira

(75) Inventor: Peter Rudolf Kolster, Boskoop (NL)

(73) Assignee: Kolster Beheer B.V., Boskoop (NL)

( * ) Notice: Subject to any disclaimer, the term of this patent is extended or adjusted under 35 U.S.C. 154(b) by 0 days.

(21) Appl. No.: 12/220,698

(22) Filed: Jul. 25, 2008

(51) Int. Cl.
*A01H 5/00* (2006.01)

(52) U.S. Cl. ..... Plt./226
(58) Field of Classification Search ..... Plt./226
See application file for complete search history.

(56) References Cited

PUBLICATIONS

Upov Plant VAriety Database 2008/06 p. 1.*

* cited by examiner

*Primary Examiner*—Annette H Para
(74) *Attorney, Agent, or Firm*—C. A. Whealy

(57) ABSTRACT

A new and distinct cultivar of *Weigela* plant named 'Kolmagira', characterized by its compact, upright and outwardly spreading plant habit; freely branching habit; yellow green and dark green variegated leaves with purple-colored margins; pink-colored flowers; and good garden performance.

2 Drawing Sheets

Botanical designation: *Weigela florida.*
Cultivar denomination: 'KOLMAGIRA'.

BACKGROUND OF THE INVENTION

The present invention relates to a new and distinct cultivar of *Weigela* plant, botanically known as *Weigela florida,* and hereinafter referred to by the name 'Kolmagira'.

The new *Weigela* is a product of a planned breeding program conducted by the Inventor in Boskoop, The Netherlands. The objective of the breeding program was to develop new compact *Weigelas* with uniquely-variegated leaves.

The new *Weigela* originated from a cross-pollination in 2001 of two unnamed seedling selections of *Weigela florida,* not patented. The new *Weigela* was discovered and selected by the Inventor as a single plant within the progeny of the stated cross-pollination in a controlled greenhouse environment in Boskoop, The Netherlands in 2005.

Asexual reproduction of the new cultivar by cuttings in Boskoop, The Netherlands since 2005 has shown that the unique features of this new *Weigela* plant are stable and reproduced true to type in successive generations of asexual reproduction.

SUMMARY OF THE INVENTION

The following traits have been repeatedly observed and are determined to be the unique characteristics of 'Kolmagira'. These characteristics in combination distinguish 'Kolmagira' as a new and distinct cultivar of *Weigela:*

1. Compact, upright and outwardly spreading plant habit.
2. Freely branching habit.
3. Yellow green and dark green variegated leaves with purple-colored margins.
4. Pink-colored flowers.
5. Good garden performance.

Plants of the new *Weigela* differ from plants of the female parent selection in the following characteristics:

1. Plants of the new *Weigela* are more vigorous than plants of the female parent selection.
2. Plants of the new *Weigela* have larger leaves than plants of the female parent selection.
3. Plants of the new *Weigela* have darker pink-colored flowers than plants of the female parent selection.

Plants of the new *Weigela* differ from plants of the male parent selection in the following characteristics:

1. Plants of the new *Weigela* are not as vigorous as plants of the male parent selection.
2. Plants of the new *Weigela* have variegated leaves whereas plants of the male parent selection do not have variegated leaves.

Plants of the new *Weigela* can be compared to plants of the *Weigela florida* 'Nana Variegata', not patented. In side-by-side comparisons in Boskoop, The Netherlands, plants of the new *Weigela* differ primarily from plants of 'Nana Variegata' in leaf coloration as plants of 'Nana Variegata' have green and white variegated leaves.

BRIEF DESCRIPTION OF THE PHOTOGRAPHS

The accompanying colored photographs illustrate the overall appearance of plants of the new *Weigela,* showing the colors as true as it is reasonably possible to obtain in colored reproductions of this type. Colors in the photographs may differ slightly from the color values cited in the detailed botanical description which accurately describe the colors of the new *Weigela.*

The photograph on the first sheet comprises a side perspective view of a typical plant of 'Kolmagira' grown in an outdoor nursery.

The photograph at the top of the second sheet is a close-up view of typical leaves of 'Kolmagira'.

The photograph at the bottom of the second sheet is a close-up view of typical flowers of 'Kolmagira'.

DETAILED BOTANICAL DESCRIPTION

Plants of the new *Weigela* have not been observed under all possible environmental conditions. The phenotype may vary somewhat with variations in environment such as temperature and light intensity, without, however, any variance in genotype. The aforementioned photographs and following observations and measurements describe plants grown during the spring and early summer in Boskoop, The Netherlands, in an outdoor nursery and under commercial production practices. During the production of the plants, day temperatures ranged from 14° C. to 32° C. and night temperatures ranged from 5° C. to 15° C. Plants were three years from planting when the photographs were taken and plants used for the description were two years from planting. In the following description, color references are made to The Royal Horticultural Society Colour Chart, 2001 Edition, except where general terms of ordinary dictionary significance are used.

Botanical classification: *Weigela florida* 'Kolmagira'.

Parentage:

*Female or seed, parent.*—Unnamed seedling selection of *Weigela florida,* not patented.

*Male or pollen, parent.*—Unnamed seedling selection of *Weigela florida,* not patented.

Propagation:

*Method.*—By cuttings.

*Time to initiate roots, summer.*—About four weeks at temperatures of 15° C. to 25° C.

*Time to initiate roots, winter.*—About seven weeks at temperatures of 5° C. to 20° C.

*Time to produce a rooted young plant, summer.*—About eight weeks at temperatures of 15° C. to 25° C.

*Time to produce a rooted young plant, winter.*—About 100 days at temperatures of 5° C. to 20° C.

*Root description.*—Fine, fibrous; pale brown in color.

*Rooting habit.*—Freely branching; moderately dense.

Plant description:

*Plant and growth habit.*—Perennial shrub. Compact, upright and outwardly spreading plant habit; broad inverted triangle. Moderate vigorous to vigorous growth habit. Freely branching habit with about eleven lateral branches developing per plant; pinching enhances lateral branch development.

*Plant height.*—About 86 cm.

*Plant diameter.*—About 93 cm.

Lateral branch description:

*Length.*—About 80 cm.

*Diameter.*—About 5 mm.

*Internode length.*—About 4 cm.

*Strength.*—Strong.

*Texture.*—Pubescent.

*Color, developing stems.*—Close to 178B.

*Color, mature stems.*—Close to N199B.

Leaf description:

*Arrangement.*—Opposite; simple.

*Length.*—About 8.1 cm.

*Width.*—About 5.5 cm.

*Shape.*—Broadly ovate to broadly obovate.

*Apex.*—Aristate.

*Base.*—Attenuate.

*Margin.*—Serrate.

*Texture, upper and lower surfaces.*—Rugose, pubescent.

*Venation pattern.*—Pinnate.

*Color.*—Developing leaves, upper surface: Centers, close to 139A; towards the margins, close to 153C to 153D; at the margin, close to 185A. Developing leaves, lower surface: Centers, close to 137B; towards the margins, close to 153C to 153D; at the margin, close to 185A. Fully expanded leaves, upper surface: Centers, close to 139A; towards the margins, close to 151C to 151D slightly tinged with close to between 163A and N163D; at the margin, close to 185A; venation, close to 146D. Fully expanded leaves, lower surface: Centers, close to 191A; towards the margins, between 146D and 151D slightly tinged with close to 163A; at the margin, close to 185A; venation, close to 146D.

*Petiole.*—Length: About 5 mm. Diameter: About 3 mm. Texture, upper and lower surfaces: Smooth, glabrous. Color, upper and lower surfaces: Close to 144A to 144B.

Flower description:

*Flower arrangement and habit.*—Campanulate flowers arranged in clusters of about eight flowers. Flowers not persistent. Flowers face upright to slightly outward. About 220 flowers develop per plant per season.

*Fragrance.*—None detected.

*Natural flowering season.*—Plants of the new *Weigela* flower from May to June in The Netherlands.

*Flower longevity.*—Flowers last about five days on the plant.

*Flower diameter.*—About 2.9 cm.

*Flower length (height).*—About 3.4 cm.

*Flower bud.*—Shape: Obovate. Length: About 2.7 cm. Diameter: About 1 cm. Color: Close to 70B.

*Corolla.*—Arrangement: Funnelform, five petals fused into a long tube with separate petal lobes. Petal lobe length: About 3.4 cm. Petal lobe width: About 9 mm. Petal lobe shape: Oblanceolate. Petal lobe apex: Obtuse. Petal lobe margin: Entire. Petal texture, upper and lower surfaces: Smooth, glabrous. Color: Petal, when opening, upper surface: Close to 70C. Petal, when opening, lower surface: Close to 72C; towards the base, close to 67C. Petal, fully opened, upper surface: Close to 75C; towards the base, close to 75B; faint yellow spot, close to 6D; color becoming closer to 70D with development. Petal, fully opened, lower surface: Close to 75A to 75B; towards the base, close to 70B.

*Sepals.*—Quantity per flower: Five. Length: About 9 mm. Width: About 1 mm. Shape: Lanceolate. Apex: Acute. Base: Cuneate. Margin: Entire. Texture, upper and lower surfaces: Smooth; glabrous. Color, upper surface: Close to 63D. Color, lower surface: Close to 63B to 63D.

*Peduncles.*—Length: About 2 cm. Diameter: About 1.5 mm. Angle: Mostly erect. Strength: Moderately strong. Texture: Smooth, glabrous. Color: Close to 146A.

*Pedicels.*—Length: About 1.2 cm. Diameter: About 1 mm. Angle: About 50° from stem axis. Strength: Moderately strong. Texture: Smooth, glabrous. Color: Between 146A to 183A to 183B.

*Reproductive organs.*—Stamens: Quantity/arrangement: Five per flower. Filament length: About 8 mm. Filament color: Close to N155B. Anther shape: Narrowly oblong. Anther length: About 3 mm. Anther color: Close to 155A. Pollen amount: Moderate. Pollen color: Close to 155A. Pistils: Quantity: One per flower. Pistil length: About 3.1 cm. Style length: About 3 cm. Style color: Close to 155A; towards the base, close to 157A. Stigma shape: Oblate. Stigma color: Close to 155A. Ovary color: Close to 143C.

*Fruits/seeds.*—Fruit and seed production have not been observed on plants of the new *Weigela*.

Garden performance: Plants of the new *Weigela* have exhibited good tolerance to rain and wind and have been observed to tolerate temperatures from about −20° C. to about 40° C.

Pathogen/pest resistance: Plants of the new *Weigela* have not been observed to be resistant to pests and pathogens common to *Weigela*.

It is claimed:

1. A new and distinct *Weigela* plant named 'Kolmagira' as illustrated and described.

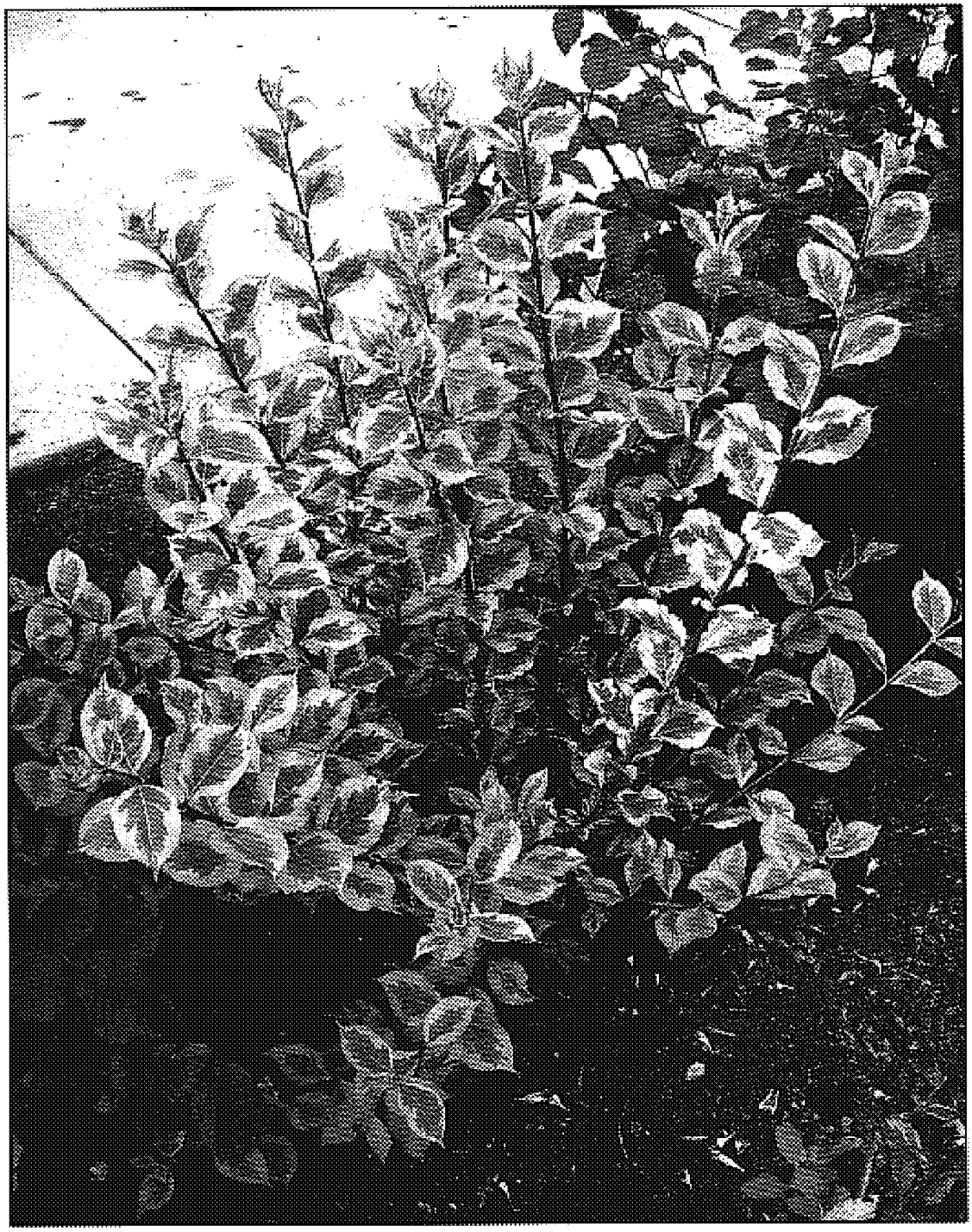

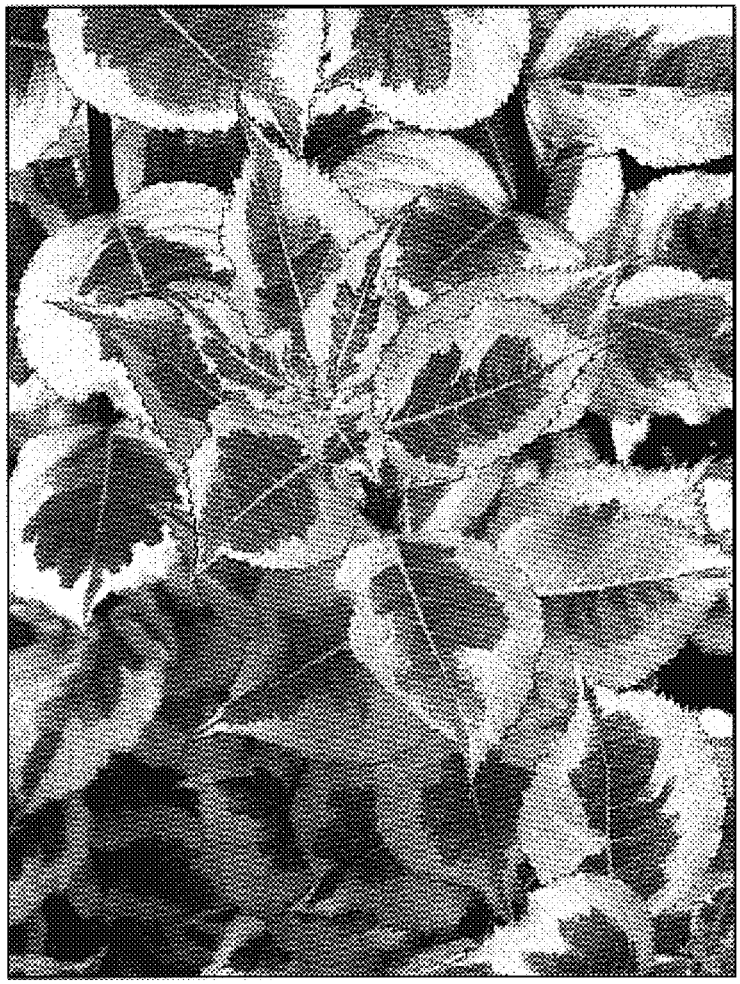
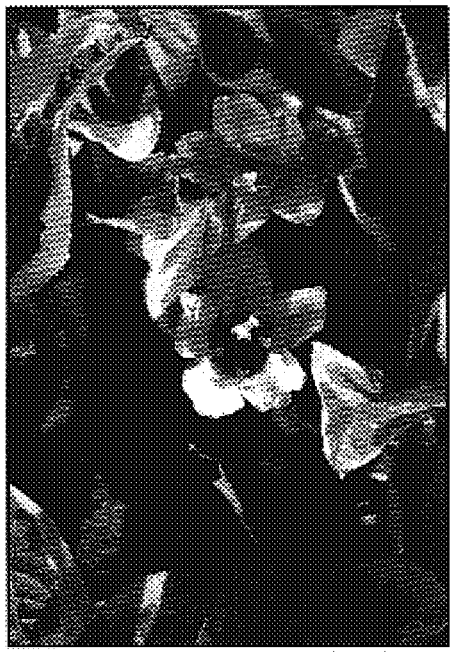

* * * * *